US007766015B2

(12) United States Patent
Harold et al.

(10) Patent No.: US 7,766,015 B2
(45) Date of Patent: Aug. 3, 2010

(54) AIR FILTERING SOFT FACE MASK

(75) Inventors: Victoria Stan Harold, Edmonton (CA); Brenda Marks, Calgary (CA); Raymond Marusyk, Edmonton (CA); Guy Plamondon, Edmonton (CA); Daniel Rossi, Edmonton (CA)

(73) Assignee: Primed Medical Products Inc., Edmonton, Alberta (CA)

( * ) Notice: Subject to any disclaimer, the term of this patent is extended or adjusted under 35 U.S.C. 154(b) by 943 days.

(21) Appl. No.: 11/592,715

(22) Filed: Nov. 3, 2006

(65) Prior Publication Data

US 2008/0105262 A1 May 8, 2008

(51) Int. Cl.
*A61M 11/00* (2006.01)

(52) U.S. Cl. ........................... 128/206.19; 128/201.17; 128/206.21

(58) Field of Classification Search ............ 128/206.19, 128/201.17, 206.21, 205.25, 205.29, 206.12, 128/206.13, 206.16
See application file for complete search history.

(56) References Cited

U.S. PATENT DOCUMENTS

| | | | | |
|---|---|---|---|---|
| 3,971,369 A | | 7/1976 | Aspelin et al. | |
| 4,014,047 A | | 3/1977 | Zobel | |
| 4,084,585 A | | 4/1978 | Venaleck | |
| 4,248,220 A | * | 2/1981 | White | 128/206.19 |
| 4,300,549 A | | 11/1981 | Parker | |
| 4,662,005 A | | 5/1987 | Grier-Idris | |
| 4,688,566 A | | 8/1987 | Boyce | |
| 5,107,547 A | | 4/1992 | Scheu | |
| 5,322,061 A | | 6/1994 | Brunson | |
| 5,553,608 A | | 9/1996 | Reese et al. | |
| 5,694,925 A | | 12/1997 | Reese et al. | |
| 5,699,791 A | | 12/1997 | Sukiennik et al. | |
| 5,699,792 A | | 12/1997 | Reese et al. | |
| 5,701,893 A | * | 12/1997 | Kern et al. | 128/206.24 |
| 5,724,964 A | | 3/1998 | Brunson et al. | |
| 5,735,270 A | | 4/1998 | Bayer | |
| 6,055,982 A | | 5/2000 | Brunson et al. | |
| 6,098,201 A | | 8/2000 | Boros, Sr. | |
| 6,098,624 A | | 8/2000 | Utamaru | |
| 6,332,465 B1 | | 12/2001 | Xue et al. | |
| 6,536,434 B1 | | 3/2003 | Bostock et al. | |
| 6,886,563 B2 | | 5/2005 | Bostock et al. | |
| 7,036,507 B2 | | 5/2006 | Jensen | |
| 7,069,930 B2 | | 7/2006 | Bostock et al. | |
| 2005/0051172 A1 | | 3/2005 | Lee | |
| 2007/0267022 A1 | * | 11/2007 | Chiam | 128/206.19 |

* cited by examiner

*Primary Examiner*—Steven O Douglas
(74) *Attorney, Agent, or Firm*—Davis & Bujold, P.L.L.C.

(57) ABSTRACT

An air filtering soft face mask has a soft body formed of multiple layers of material, including at least one layer of air filtering material capable of filtering selected contaminants from air. The body has an arcuate or peaked nose engaging edge adapted to engage a nose of a wearer and terminating in remote ends that extend downwardly. The body has a chin underlying edge adapted to underlie a chin of a wearer and terminating in remote ends that extend upwardly. The remote ends of the chin underlying edge being secured to the remote ends of the nose engaging edge to form side edges. Jaw movement tensions the body, forcing the nose engaging edge into firmer engagement with the nose of the wearer, forcing the chin underlying edge into firmer engagement with the chin of the wearer and tensioning the side edges into firmer engagement with the cheeks of the wearer.

17 Claims, 4 Drawing Sheets

AIR FILTERING SOFT FACE MASK

FIELD

The present invention relates to a soft face mask (as opposed to a rigid face mask) made of a filtering material that filters contaminants and is used for medical or industrial use.

BACKGROUND

Air filtering face masks are either soft or rigid. In order to be effective they must form an air seal, so that all air entering and exiting the mask passes through filtering material. Soft face mask made of filtering material have a limited ability to adjust to various facial sizes and shapes, as they can not accurately follow facial contours in the same manner as rigid face masks. The problem is exacerbated by movement of a wearer's jaw. Downward movement of the wearer's jaw, as a result of talking or coughing, exerts a downward force, causing gaps to form along edges of the mask which compromise the air seal. This allows airborne contaminants to bypass the filtering material, entering and exiting the mask via the gaps along the edges, thereby defeating the intended respiratory protection.

SUMMARY

There is provided an air filtering soft face mask which has a soft body formed of multiple layers of material, including at least one layer of air filtering material capable of filtering selected contaminants from air. The body has an arcuate or peaked nose engaging edge adapted to engage a nose of a wearer and terminating in remote ends that extend downwardly. The body has a chin underlying edge adapted to underlie a chin of a wearer and terminating in remote ends that extend upwardly. The remote ends of the chin underlying edge are secured to the remote ends of the nose engaging edge to form side edges. Jaw movement tensions the body, forcing the nose engaging edge into firmer engagement with the nose of the wearer, forcing the chin underlying edge into firmer engagement with the chin of the wearer and tensioning the side edges into firmer engagement with the cheeks of the wearer.

BRIEF DESCRIPTION OF THE DRAWINGS

These and other features of the invention will become more apparent from the following description in which reference is made to the appended drawings, the drawings are for the purpose of illustration only and are not intended to in any way limit the scope of the invention to the particular embodiment or embodiments shown, wherein.

DETAILED DESCRIPTION

Figure 1:
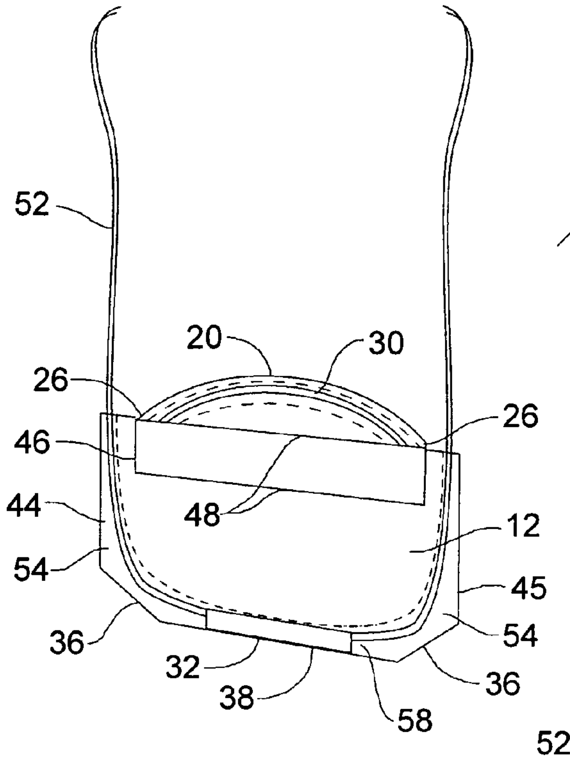
FIG. 1 is a partially transparent (showing ties) perspective view of the air filtering soft face mask.

The preferred embodiment, an air filtering soft face mask generally identified by reference numeral 10, will now be described with reference to FIG. 1 through 5.

Figure 2:
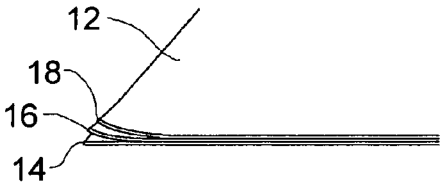
FIG. 2 is a perspective view of the body of the air filtering soft face mask showing the different layers of material.
Figure 3:
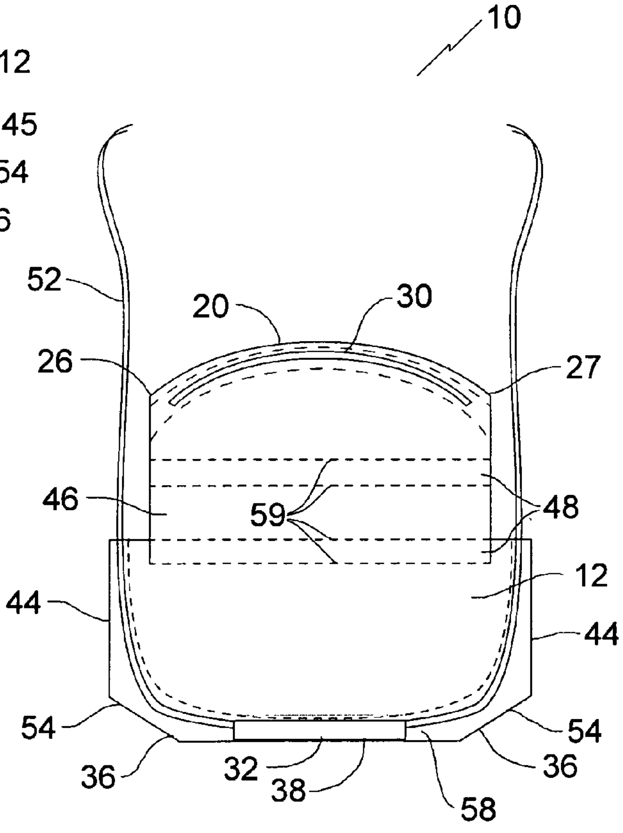
FIG. 3 is a partially transparent (showing ties) front elevation view of the air filtering soft face mask of FIG. 1, as it would appear prior to folding and sewing.
Figure 4:
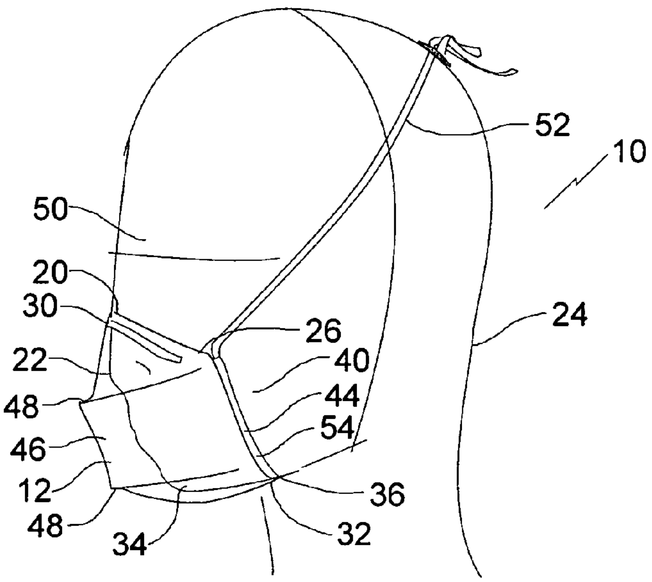
FIG. 4 is a side elevation view of a wearer wearing the air filtering soft face mask of FIG. 1.
Figure 5:
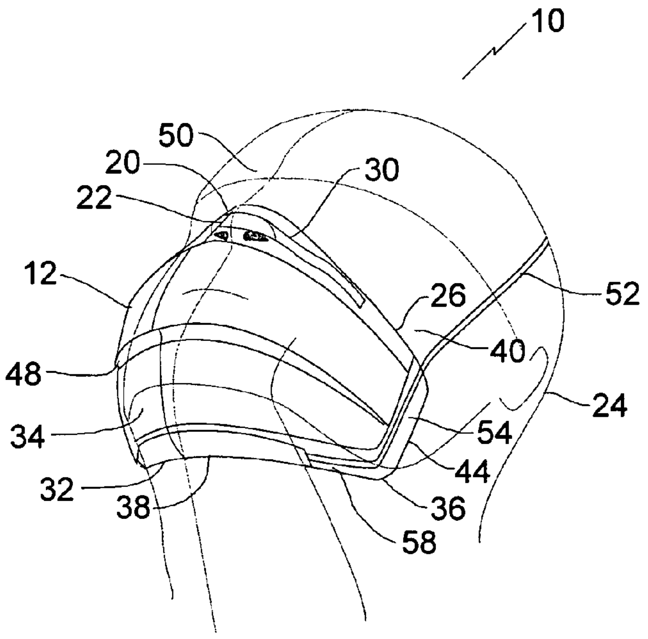
FIG. 5 is a partially transparent (showing facial detail) lower perspective view of a wearer wearing the air filtering soft face mask of FIG. 1.

Structure and Relationship of Parts:

Referring to FIG. 1, air filtering soft face mask 10 includes a soft body 12. Referring to FIG. 2, body 12 is formed of multiple layers 14, 16, and 18 of material. At least one layer, generally middle layer 16, is made from air filtering material capable of filtering selected contaminants from air. Additionally, one of the layers may be treated with an antimicrobial agent. Referring again to FIG. 1, body 12 has an arcuate or peaked nose engaging edge 20 along its top that terminates in remote ends 26. Referring to FIG. 4, nose engaging edge 20 is adapted to engage a nose 22 of a wearer 24, with remote ends 26 extending downwardly across cheeks 40 of wearer 24. Referring to FIG. 5, a malleable semi-rigid reinforcement strip 30 is secured to body 12 along nose engaging edge 20, and is adapted to be shaped to fit nose 22 of wearer 24. Along the bottom, body 12 has a chin underlying edge 32 that underlies a chin 34 of wearer 24. Chin underlying edge 32 terminates in remote ends 36 that extend upwardly across the cheeks 40 of wearer 24. As depicted, chin underlying edge 32 also has a perspiration absorbing band 38. Referring to FIG. 1, remote ends 36 of chin underlying edge 32 are secured to remote ends 26 of nose engaging edge 20 to form side edges 44. Referring to FIG. 4, any jaw movement by wearer 24 tensions body 12, which forces nose engaging edge 20 into firmer engagement with nose 22, forces chin underlying edge 32 into firmer engagement with chin 34 and tensions side edges 44 into firmer engagement with cheeks 40. Between nose engaging edge 20 and chin underlying edge 32, an expandable breathing pocket 46 is positioned. Referring to FIG. 1, pocket 46 is formed from pleats 48 in body 12. Referring to FIG. 3, body 12 is folded along fold lines 59 to form pleats 48, and the sides of pocket 46 are then sewn or otherwise secured. Thus, pocket 46 may be pushed outward to form a breathing space within body 12. Pocket 46 could also be formed using other techniques known in the art. Referring to FIG. 4, body 12 is attached to the face 50 of wearer 24 by a strap 52 that provides tension to side edges 44. This may be done by providing a strap 52 that extends along a bottom channel 58 in chin underlying edge 32 and up through side channels 54 in side edges 44.

Operation:

Referring to FIG. 4, mask 10 is positioned on face 50 of wearer 24 by placing body 12 such that nose engaging edge 20 engages nose 22, such that remote ends 26 of nose engaging edge 20 extend downwardly across cheeks 40. Pressure is then applied to reinforcement strip 30 to mold it to the shape of nose 22. Chin underlying edge 32 is then positioned below chin 34 such that remote ends 36 of chin underlying edge 32 extend upwardly across cheeks 40. Strap 52 is then secured to wearer 24, such that chin underlying edge 32 and side edges 44 are in tension. Once correctly positioned, any jaw movement, caused by talking or coughing for example, tensions body 12, which in turn forces nose engaging edge 20 into firmer engagement with nose 22, forces chin underlying edge 32 into firmer engagement with chin 34, and tensions side edges 44 into firmer engagement with cheeks 40 of wearer 24.

Figure 6:
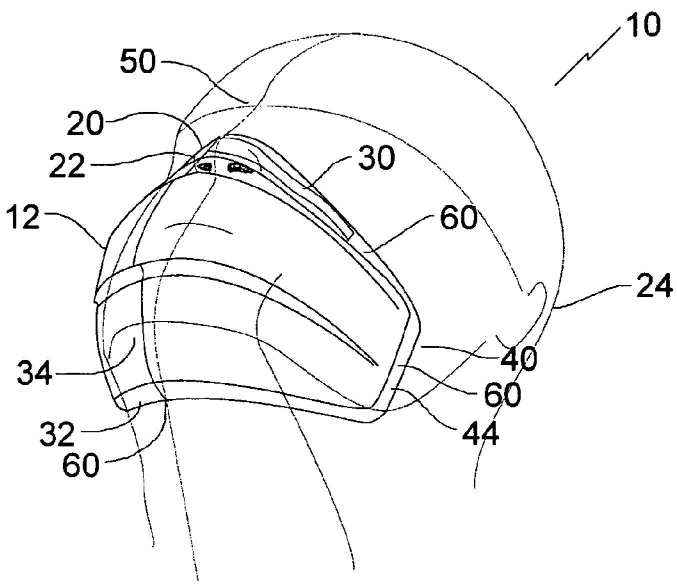
FIG. 6 is a partially transparent (showing facial detail) lower perspective view of that wearer wearing a variation of the air filtering soft face mask of FIG. 1.
Figure 7:
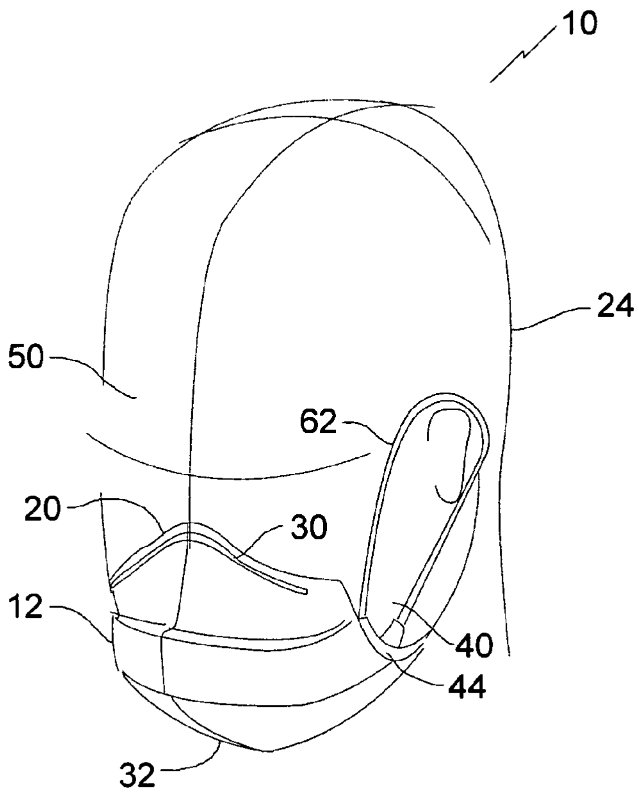
FIG. 7 is an upper perspective view of a further variation of the air filtering soft face mask of FIG. 1.
Figure 8:
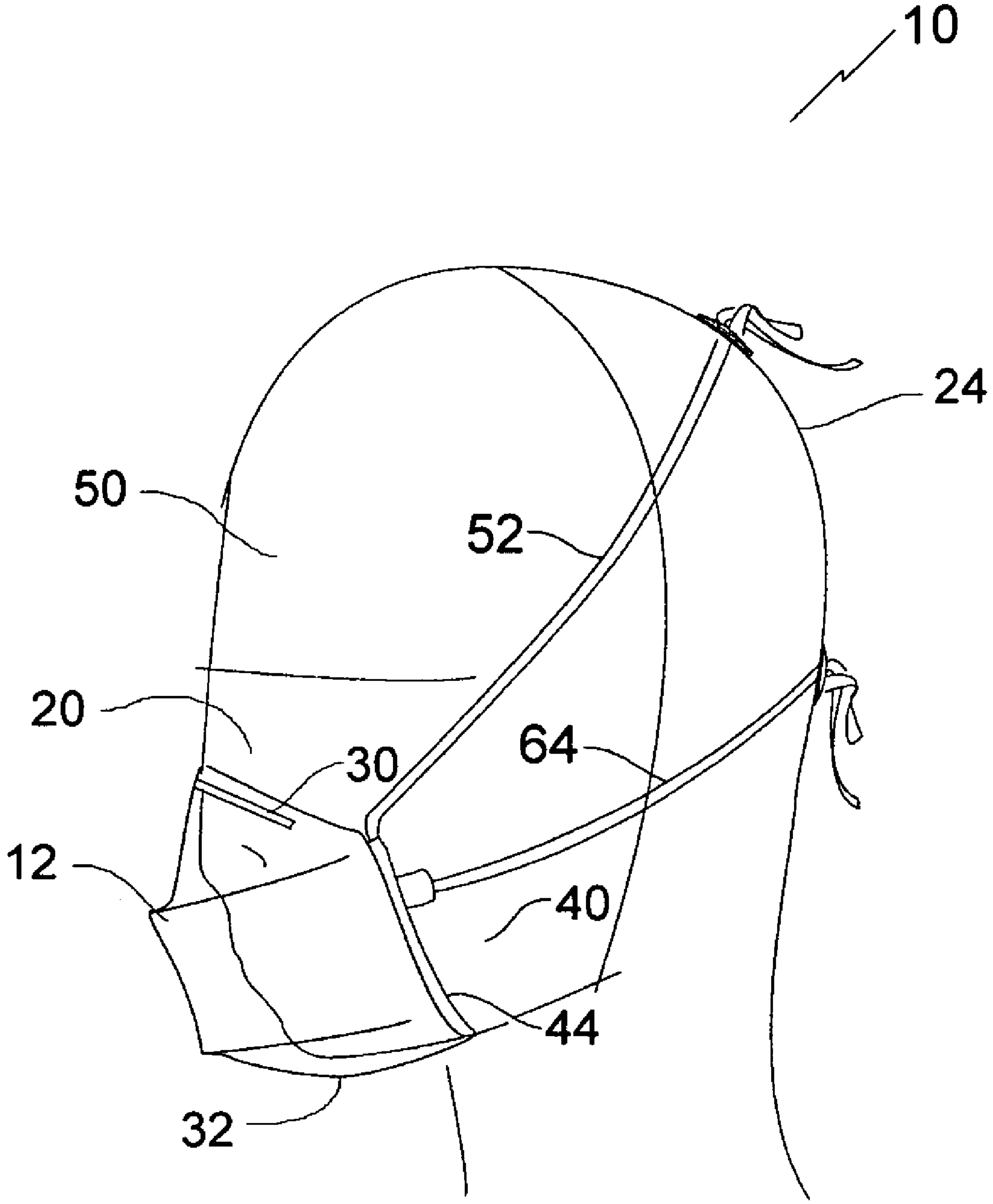
FIG. 8 is a partially transparent (showing facial detail) side elevation view of a further variation of the air filtering soft face mask of FIG. 1.

Variations:

The manner of attachment to the face of the wearer is not critical. Referring to FIG. 6 through 8, variations of ways in which body 12 may be attached to face 50 of wearer 24 are shown. Referring to FIG. 6, adhesive 60 positioned on nose engaging edge 20, side edges 44 and chin underlying edge 32, such that body 12 adheres directly to nose 22, cheeks 40, and chin 34 of wearer 24. Referring to FIG. 7, another option is to provide ear loops 62 that pass over the ears 64 of wearer 24. Straps 62 would be connected to body 12 similar to strap 52 described above, with end 66 connected to side edges 44 to form a loop. Alternatively, referring to FIG. 8, an additional tie strap 64 connected to side edges 44 may be included, in addition to strap 52 described above, to more securely hold body 12 against face 50.

The term contaminants must be interpreted in light of the intended application for the mast. In a wood working shop, air borne contaminants may be saw dust. In a spray booth of a paint shop, the air borne contaminants may be paint spray. In a hospital or medical laboratory, the air borne contaminants may be micro-organisms.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

It will be apparent to one skilled in the art that modifications may be made to the illustrated embodiments without departing from scope of the claims.

What is claimed is:

1. An air filtering soft face mask, comprising:

a soft body formed of multiple layers of material including at least one layer of air filtering material capable of filtering selected contaminants from air;

the body having an arcuate or peaked nose engaging edge adapted to engage a nose of a wearer and terminating in remote ends that extend downwardly;

the body having a chin underlying edge adapted to underlie a chin of a wearer and terminating in remote ends that extend upwardly;

the remote ends of the chin underlying edge being secured to the remote ends of the nose engaging edge to form side edges, such that jaw movement tensions the body forcing the nose engaging edge into firmer engagement with the nose of the wearer, forcing the chin underlying edge into firmer engagement with the chin of the wearer and tensioning the side edges into firmer engagement with the cheeks of the wearer; and means for attaching the body to a face of the wearer.

2. The air filtering soft face mask of claim 1, wherein a malleable semi-rigid reinforcement strip is secured to the body along the nose engaging edge, the reinforcement strip being adapted to be shaped to fit the nose of the wearer.

3. The air filtering soft face mask of claim 1, wherein the body has an expandable breathing pocket positioned between the nose engaging edge and the chin underlying edge.

4. The air filtering soft face mask of claim 3, wherein the expandable breathing pocket is formed from pleats or folds in the body.

5. The air filtering soft face mask of claim 1, wherein each of the multiple layers consists of a single sheet of material.

6. The air filtering soft face mask of claim 1, wherein the means for attaching the body to a face of the wearer is adhesive.

7. The air filtering soft face mask of claim 1, wherein the means for attaching the body to a face of the wearer is at least one tie strap.

8. The air filtering soft face mask of claim 1, wherein the means for attaching the body to a face of the wearer is a single tie strap positioned along the chin underlying edge and up the sides edges.

9. The air filtering soft face mask of claim 1, wherein the means for attaching the body to a face of the wearer is ear loops.

10. The air filtering soft face mask of claim 1, wherein at least one of the multiple layers of the body is treated with an antimicrobial agent.

11. An air filtering soft face mask, comprising:

a soft body formed of multiple layers of material including at least one layer of air filtering material capable of filtering selected contaminants from air;

the body having an arcuate or peaked nose engaging edge adapted to engage a nose of a wearer and terminating in remote ends that extend downwardly across cheeks of the wearer;

a malleable semi-rigid reinforcement strip secured to the body along the nose engaging edge, the reinforcement strip being adapted to be shaped to fit the nose of the wearer;

the body having a chin underlying edge adapted to underlie a chin of a wearer and terminating in remote ends that extend upwardly across a cheek of the wearer;

an expandable breathing pocket positioned between the nose engaging edge and the chin underlying edge, the expandable breathing pocket being formed from pleats or folds in the body;

the remote ends of the chin underlying edge being secured to the remote ends of the nose engaging edge to form side edges, such that jaw movement tensions the body forcing the nose engaging edge into firmer engagement with the nose of the wearer, forcing the chin underlying edge into firmer engagement with the chin of the wearer and tensioning the side edges into firmer engagement with the cheeks of the wearer; and means for attaching the body to a face of the wearer.

12. The air filtering soft face mask of claim 11, wherein the means for attaching the body to a face of the wearer is adhesive.

13. The air filtering soft face mask of claim 11, wherein the means for attaching the body to a face of the wearer is at least one tie strap.

14. The air filtering soft face mask of claim 11, wherein the means for attaching the body to a face of the wearer is ear loops.

15. The air filtering soft face mask of claim 11, wherein the means for attaching the body to a face of the wearer is a single tie strap positioned along the chin underlying edge and up the sides edges.

16. The air filtering soft face mask of claim 11, wherein at least one of the multiple layers of the body is treated with an antimicrobial agent.

17. The air filtering soft face mask of claim 11, wherein the chin underlying edge has an perspiration absorbing band.

* * * * *